United States Patent [19]
Lowe, III

[11] Patent Number: 5,373,003
[45] Date of Patent: Dec. 13, 1994

[54] 1-AZABICYCLO[3.2.2]NONAN-3-AMINE DERIVATIVES

[75] Inventor: John A. Lowe, III, Stonington, Conn.

[73] Assignee: Pfizer Inc., New York, N.Y.

[21] Appl. No.: 108,735

[22] PCT Filed: Jan. 17, 1992

[86] PCT No.: PCT/US92/00113
§ 371 Date: Aug. 27, 1993
§ 102(e) Date: Sep. 24, 1993

[51] Int. Cl.$^5$ .................. A61K 31/55; A61K 31/435; C07D 471/08; C07D 221/00
[52] U.S. Cl. ...................................... 514/216; 540/584
[58] Field of Search ......................... 540/584; 514/216

[56] References Cited
U.S. PATENT DOCUMENTS

| | | | |
|---|---|---|---|
| 3,560,510 | 2/1971 | Warawa | 546/133 |
| 4,775,668 | 10/1988 | Jefson et al. | 514/216 |
| 4,910,193 | 3/1990 | Buchheit | 574/216 |
| 5,106,843 | 4/1992 | Ward et al. | 514/216 |
| 5,202,318 | 4/1993 | Berger et al. | 540/584 |

*Primary Examiner*—Joseph E. Evans
*Attorney, Agent, or Firm*—Peter C. Richardson; Paul H. Ginsburg

[57] ABSTRACT

The present invention relates to novel 1-azabicyclo[3.2.2]nonan-3-amine derivatives of the formula

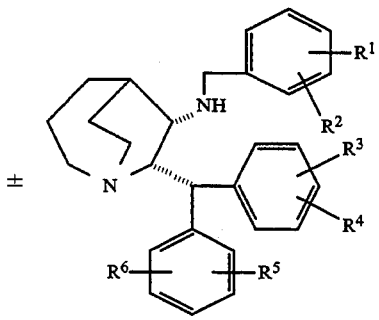

wherein $R^1$, $R^2$, $R^3$, $R^4$, $R^5$ are each independently selected from hydrogen, fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety, and benzoyloxycarbonyl. These compounds are useful in the treatment of inflammatory and central nervous system disorders, as well as other disorders.

11 Claims, No Drawings

1-AZABICYCLO[3.2.2]NONAN-3-AMINE DERIVATIVES

BACKGROUND OF THE INVENTION

This invention relates to novel 1-azabicyclo[3.2.2]-nonan-3-amine derivatives.

The compounds of the invention have the ability to antagonize substance P. They are, therefore, useful in treating conditions such as intestinal disorders, central nervous system disorders, inflammatory diseases, pain and migraine. The present invention also relates to pharmaceutical compositions comprising such compounds and to the use of such compounds in treating the foregoing conditions.

E. J. Warawa in U.S. Pat. No. 3,560,510 refers to certain 3-amino-2-benzhydrylquinuclidines as being useful as diuretic agents, with the corresponding unsubstituted 3-benzylamino compounds acting as intermediates for same. Additionally, E. J. Warawa et al. In the Journal of Medicinal Chemistry, Vol. 18, p. 587 (1975) extends this work to other members of the series wherein the 3-amino moiety is either ethylamino, beta-phenylethylamino, beta-isopropyl-amino or 2-furfurylamino, but in no instance is there any substitution on the phenyl group itself and the 2-benzhydryl moiety is always symmetrically substituted (or unsubstituted). Neither of the aforementioned documents teaches or suggests any of these compounds to be useful as substance P antagonists.

PCT Patent Application PCS/US 89/05338, filed Nov. 20, 1989, now Published PCT International Patent Application No. WO090/05729 (published May 31, 1990) in addition to also being U.S. Pat. No. 5,162,339, refers to cis-3-[(cyclic)methylamino]-2-[(alpha-substituted)arylmethyl]quinuclidines, 3-[(cyclic)methylamino]-2-[(alpha-substituted)arylmethyl]quinuclidines and cis-3-[(cyclic)methyleneamino]-2-[alpha-substituted)-arylmethyl]quinuclidinesandstates that they are useful as substance P antagonists. PCT Patent Application PCT/US 90/00116, now Published PCT International Patent Application No. WO91/09844 (published Jul. 7, 1991), refers to carbotricyclic ring systems wherein one of the rings is substituted with an amino group and wherein one carbon atom in each of two of the rings may be replaced by a hetero atom, and states that they are useful as substance P antagonists.

U.S. patent application Ser. No. 07/557,442 filed Jul. 23, 1990 and now abandoned in favor of continuation-in-part U.S. patent application Ser. No. 988,125, filed May 14, 1991, which corresponds to PCT Patent Application PCT/US/91/03369, filed May 15, 1991 and now Published PCT International Patent Application No. WO092/01688 (published Feb. 6, 1992), refers to azatricyclic quinuclidine derivatives and states that such compounds are useful as substance P antagonists.

Substance P is a naturally occurring undecapeptide belonging to the tachykinin family of peptides, the latter being so-named because of their prompt stimulatory action on smooth muscle tissue. More specifically, substance P is a pharmacologically-active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseased has been amply demonstrated in the art. For instance, substance P has recently been shown to be involved in the transmission of pain or migraine [see B. E. B. Sandberg et al., Journal of Medicinal Chemistry, Vol. 25, p. 1009 (1982)], as well as in central nervous system disorders such as anxiety and schizophrenia, in respiratory and inflammatory diseases such as asthma and rheumatoid arthritis, respective, and in gastrointestinal disorders and diseases of the GI tract, like ulcerative colitis and Crohn's disease, etc. (see D. Regoli in "Trends in Cluster Headache," πEdited by F. Sicuteri et al., Elsevier Scientific Publishers, Amsterdam, 1987, pp. 85-95).

SUMMARY OF THE INVENTION

The present invention relates to compounds of the formula

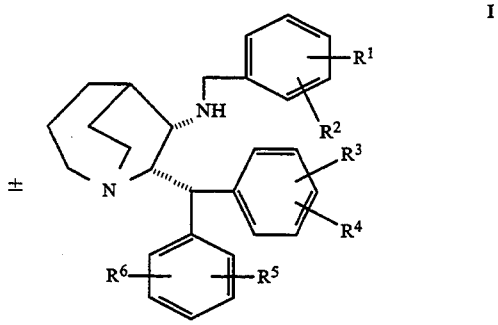

I wherein $R^1$, $R^2$, $R^3$, $R^4$, $R^5$, and $R^6$ are each independently selected from hydrogen fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety, and benzoyloxycarbonyl; and the pharmaceutically acceptable salts of such compounds.

Examples of compounds of the formula I include:

2-(Diphenylmethyl)-N-((2,4-dimethoxyphenyl)methyl)-1-azabicyclo[3.2.2]nonan-3-amine;

2-(Diphenylmethyl)-N-((2,5-dimethoxyphenyl)methyl)-1-azabicyclo[3.2.2]nonan-3-amine;

2-(Diphenylmethyl)-N-((2-methoxy, 5-chlorophenyl)methyl)-1-azabicyclo[3.2.2]nonan-3-amine;

2-(Diphenylmethyl)-N-((2-methoxy, 5-fluorophenyl)methyl)-1-azabicyclo[3.2.2]nonan-3-amine;

2-(Di(4-fluorophenyl)methyl)-N-((2-methoxyphenyl)methyl)-1-azabicyclo[3.2.2]nonan-3-amine;

2-(Di(4-fluorophenyl)methyl)-N-((2,4-dimethoxyphenyl)methyl)-1-azabicyclo[3.2.2]nonan-3-amine;

2-((2-Fluorophenyl), (3-fluorophenyl)methyl)-N-((2-methoxyphenyl)methyl)-1-azabicyclo[3.2.2]nonan-3-amine;

2-(Di(3-fluorophenyl)methyl)-N-((2,4-dimethoxyphenyl)methyl)-1-azabicyclo[3.2.2]non-3-amino; and 2-(Diphenylmethyl)-N-((2-chlorophenyl)methyl)-1-azabicyclo[3.2.2]nonan-3-amine.

A preferred compound of the formula I is 2-(diphenylmethyl)-N-((2-methoxyphenyl)methyl-1-azabicyclo[3.2.2]nonan-3-amine).

The present invention also relates to a pharmaceutical composition for treating or preventing a condition selected from the group consisting of inflammatory diseases (e.g., arthritis, psoriasis, asthma and inflammatory and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophillic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis disorders related to immune enhancement or suppression such as systemic lupus erythematosus, and rheumatic diseases such as fibrostis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as sceroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g. arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment of prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formula I have chiral centers and therefore exist in different enantiomeric forms. This invention relates to all optical isomers and all stereoisomers of compounds of the formula I, and mixtures thereof.

Optically active compounds of the formula I are additionally useful as synthetic intermediates in the preparation of the corresponding racemic mixtures and opposite enantiomers.

Formulae I and VII above include compounds identical to those depicted but for the fact that one or more hydrogen or carbon atoms are replaced by radioactive isotopes thereof (e.g., tritium, nitrogen-15 or carbon-13 isotopes thereof). Such radiolabelled compounds are useful as research and diagnostic tools in metabolism pharmakinetic studies and in binding assays. Specific applications in research include radioligand binding assays, autoradiography studies and in vivo binding studies, while specific applications in the diagnostic area include studies of the substance P receptor in the human brain in in vivo binding in the relevant tissues for inflammation, e.g. immune-type cells or cells that are directly involved in inflammatory bowel disorders and the like.

DETAILED DESCRIPTION OF THE INVENTION

The compounds of the formula I may be prepared as described in the following reaction scheme and discussion. Unless otherwise indicated, in the reaction scheme and discussion that follow, $R^1$, $R^2$, $R^3$, $R^4$, $R^5$ and $R^6$ are defined as above.

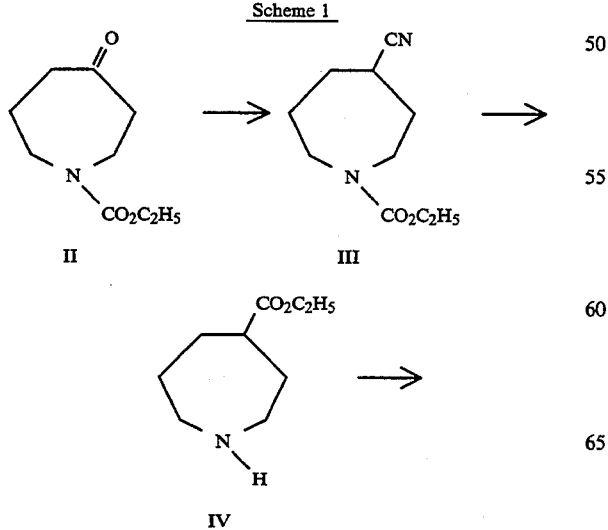

Scheme 1

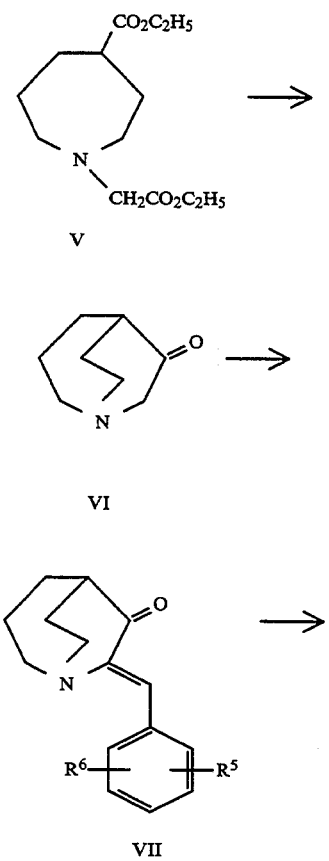

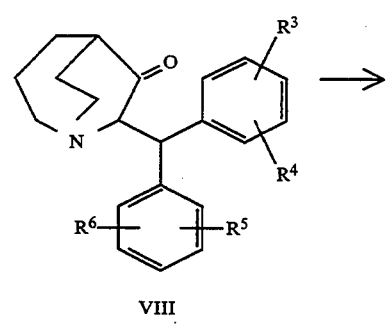

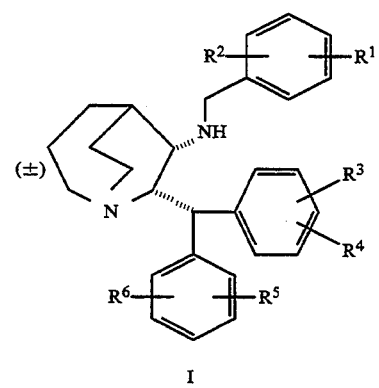

Scheme 2

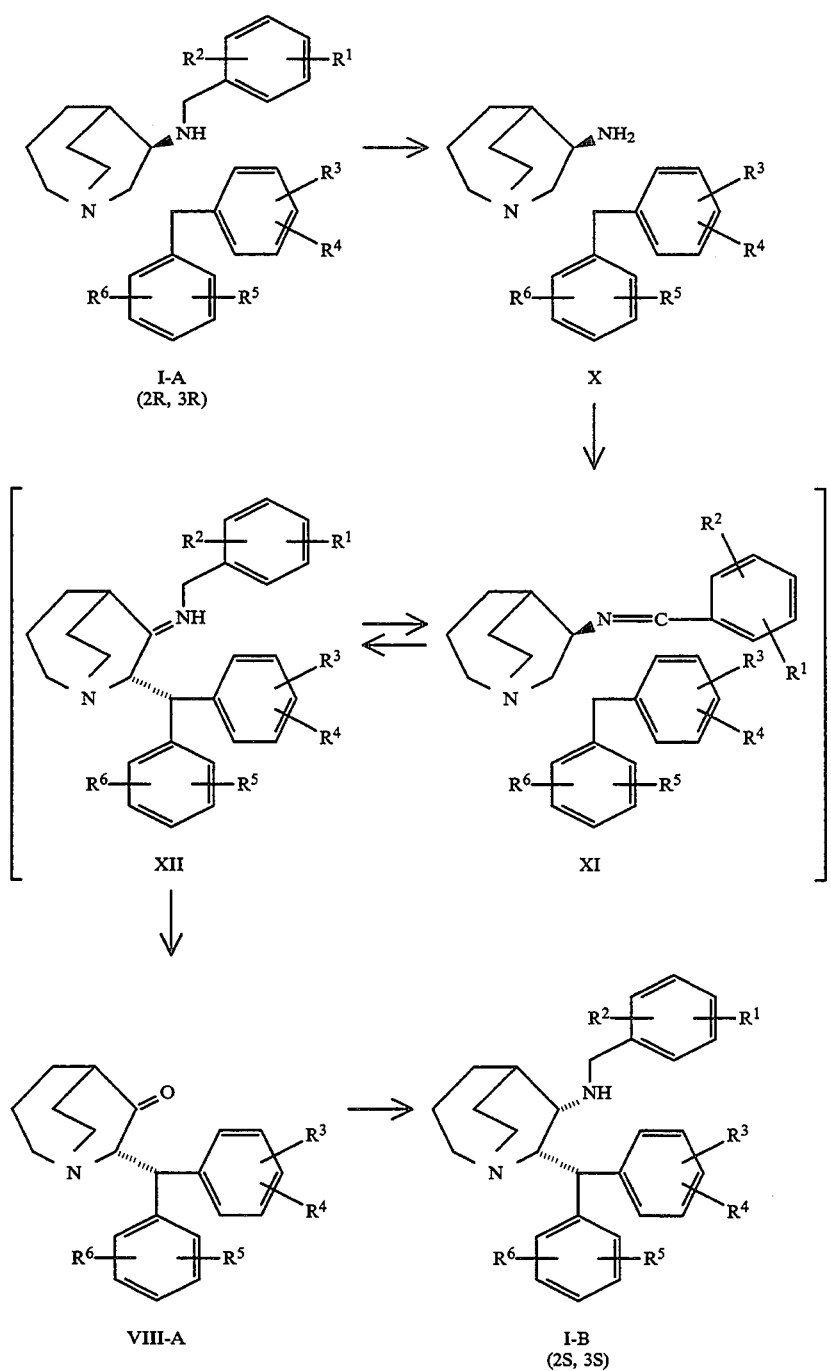

Referring to scheme 1, N-carboethoxyperhydroazepin-4-one (II) is reacted with tosylmethylisocyanide in an inert solvent such as glyme or another ethereal solvent, or a protic, a polar solvent such as dimethylsulfoxide, in the presence of a base such as an alkali metal alkoxide, for about 10 minutes to 24 hours. Preferably, the solvent is glyme and the reaction is carried out in the presence of ethanol and potassium t-butoxide for about 18 hours. This reaction is generally conducted at a temperature from about $-50°$ C. to about the reflux temperature of the solvent, and is preferably conducted at about 60° C.

The foregoing reaction produces the compound 4-cyano-N-carboethoxyperhydroazepine (III), which is then converted to ethylperhydroazepine-4-carboxylate (IV) by reacting it with a mineral acid, sulfuric acid or phosphoric acid, preferably hydrochloric acid. Generally, this reaction is conducted in a lower alcohol solvent, preferably ethanol, at a temperature from about room temperature to about the reflux temperature of the solvent, preferably at the reflux temperature of the solvent, for about 10 minutes to about 24 hours, preferably about 18 hours.

Treatment of ethyl perhydroazepine-4-carboxylate (IV) with an alkanoylmethyl halide, preferably ethylbromoacetate, in the presence of a soluble organic base such as a tertiary alkyl amine (e.g., triethylamine), produced ethyl-N-ethoxycarbonylmethylperhydroazepine-4-carboxylate (V). Suitable solvents for this reaction include lower alcohols, with ethanol being preferred. The reaction temperature may range from about room temperature to about the reflux temperature of the solvent, and is preferably the reflux temperature of the solvent. This reaction is usually carried out for about 10 minutes to 100 hours, preferably about 18 hours.

The ethyl-N-ethoxycarbonylmethylperhydroazepine-4-carboxylate (V) obtained in the above step is then converted to 1-azabicyclo[3.2.2]nonan-3-one (VI) by reacting it with an alkali or alkaline earth metal alkoxide, preferably potassium ethoxide. Suitable reaction inert solvents for this reaction include hydrocarbon solvents such as hexane, benzene and toluene. Suitable reaction temperature range from about room temperature to about the reflux temperature of the solvent. The reflux temperature is preferred. The solvent is then evaporated and the residue taken up in a mineral acid such as dilute hydrochloric or dilute sulfuric acid. An ethereal hydrocarbon solvent such as dioxane may optionally be used as a co-solvent. Preferably, this reaction is conducted at the reflux temperature of the solvent, but temperature ranging from about room temperature to about the reflux temperature are also suitable.

The desired compound of the formula VII is obtained by treating 1-azabicyclo[3.2.2]nonan-3-one with the appropriate compound of the formula

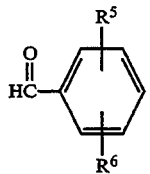

This reaction is typically carried out in a reaction inert aqueous or organic solvent. Suitable solvents include water, lower alcohols, ether, tetrahydrofuran (THF), dimethylformamide (DMF), benzene, toluene, hexane, methylene chloride and chloroform. Ethanol is the preferred solvent. Preferably, the reaction is run in the presence of a basic catalyst. Sodium hydroxide is the preferred catalyst, but other bases such as alkali and alkaline earth metal hydroxides, carbonates and alkoxides, as well as organic amine bases such as trialkylamines and pyridine may also be used. Generally, the reaction is run for about 10 minutes to about 24 hours. The reaction temperature may range from about 0° C. to about 200° C., and is preferably about the reflux temperature of the solvent.

The compound of formula VII so obtained is then reacted with a compound of the formula $(R^3)(R^4)C_6H_3MgX$ wherein X is chloro, bromo or iodo, to form a compound of the formula VIII. This reaction is usually carried out in a reaction inert hydrocarbon, chlorohydrocarbon or ethereal solvent such as benzene, ether, toluene, hexane, THF or ethyl acetate. The preferred solvent is ether. The reaction is usually run for about 1 minute to about 10 hours. Suitable reaction temperatures range from about −70° C. to about 100° C., with about 0° C. being preferred.

The compound of formula VIII is then converted to the corresponding desired compound of the formula I by reacting it with a compound of the formula

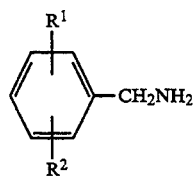

and then treating the reaction mixture with a reducing agent.

The reaction of the compound of formula VIII with the above amine of formula IX is typically carried out in a reaction inert hydrocarbon or chlorohydrocarbon solvent in the presence of an acidic catalyst. Examples of solvents that may be used include hexane, benzene, toluene, chloroform, methylene chloride, ether, THF, and ethyl acetate. Examples of catalysts that may be used include mineral acids, titanium trichloride, molecular sieves and organic acids such a camphor sulfonic acid. Toluene is the preferred solvent and camphor sulfonic acid is the preferred catalyst. This reaction is generally conducted over a period of about 0.5 hours to about 24 hours, at a temperature from about room temperature is about 110° C. The reflux temperature of the solvent is preferred.

The reaction mixture is then treated with a reducing agent, as indicated above, to obtain the desired compound of formula I. Reducing agents that may be used include 9-borobicyclononane (9-BBN), triethylsilane and metal hydrides such as sodium borohydride and sodium triacetoxyborohydride. The preferred reducing agent is 9-BBN. Generally, the reduction is carried out in a reaction inert hydrocarbon, chlorohydrocarbon, carboxyhydrocarbon, aqueous or alcoholic solvent. Water, lower alcohols, trifluoroacetic acid, benzene, toluene, ether, hexane, THF, ethyl acetate and chloroform are suitable, with THF being preferred when the reducing agent is 9-BBN. The preferred reaction temperature is about room temperature, but the reduction may be carried out at temperatures ranging from about room temperature to about 200° C.

The 2R,3R enantiomers of the compounds of formula I may be converted into the corresponding 2S,3S enantiomers by the following procedure, which is illustrated in Scheme 2.

Referring to scheme 2, the 2R,3R enantiomer having the formula I-A is treated with hydrogen in the presence of a metal containing catalyst such as platinum or palladium. Generally, this reaction is conducted in a reaction inert solvent such as acetic acid or a lower alcohol, at a temperature from about 0° C. to about 50° C. Preferably, the compound of formula I-A is treated with hydrogen in the presence of palladium on carbon in a mixture of methanol/ethanol in water or methanol/ethanol containing hydrochloric acid at a temperature of about 25° C.

The above reaction yields an amine having the formula X. This amine is then reacted with a compound of the formula $R^1CHO$ in the presence of a drying agent or using an apparatus designed to remove azeotropically the water generated, to produce an imine of the formula XI. The preparation of the imine is generally carried out in a reaction inert solvent such as benzene, xylene or toluene, preferably toluene, at a temperature from about 25° C. to about 110° C., preferably at about the reflux temperature of the solvent. Suitable drying agents/solvent system include titanium tetrachloride/dichloromethane, titanium isopropoxide/dichloromethane and molecular sieves/THF. Titanium tetrachloride/dichloromethane is preferred.

The resulting imine of formula XI is then converted to the corresponding isomeric imine having the formula XII by reacting it with a strong base such as lithium N,N-diisopropylamide or t-butyllithium. An equilibrium between the imines of formulae XI and XII results. This reaction is typically conducted in an ethereal solvent such as THF or ethyl ether, at a temperature from about $-78°$ C. to about the reflux temperature of the solvent. It is preferably conducted at the reflux temperature. Hydrolysis of the imine of formula XII yields the corresponding ketone having the formula VIII-A. The hydrolysis is preferably conducted using a mineral acid such as hydrochloric or sulfuric acid, at a temperature from about 0° C. to about 100° C.

The ketone of formula VIII-A formula in the preceding step may be converted to the corresponding 2S,3S enantiomer of formula I-B by the procedure described above and depicted in scheme 1 for converting compounds of the formula VIII into compounds of the formula I.

In each of the reactions discussed or illustrated in schemes 1 to 4 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula I and the pharmaceutically acceptable salts thereof are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The compounds of Formula I and their pharmaceutically acceptable salts exhibit substance P receptor-binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reyanud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The compounds of the formula I and the pharmaceutically acceptable salts thereof can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention as substance P antagonists is determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a $-70°$ C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at $30,000 \times G$ for a period of 20 minutes. The pellet is resuspended in 50 volumes of Tris buffer, rehomogenized and then recentrifuged at $30,000 \times G$ for another twenty-minute period. The pellet is then resuspended in 40 volumes of ice-cold 50 mM Tris buffer (pH 7.7) containing 2 mM of calcium chloride, 2 mM of magnesium chloride, 40 g/ml of bacitracin, 4 μg/ml of leupeptin, 2 μg of chymostatin and 200 g/ml of bovine serum albumin. This step completes the production of the tissue preparation.

The radioligand binding procedure is then carried out in the following manner, viz., by initiating the reaction via the addition of 100 μl of the test compound made up to a concentration of 1 μM, followed by the addition of 100 μl of radioactive ligand made up to a final concentration 0.5 mM and then finally by the addition of 800 μl of the tissue preparation produced as described above. The final is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four time with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The anti-psychotic activity of the compounds of the present invention as neuroleptic agents for the control of various psychotic disorders is determined primarily by a study of their ability to suppress substance P-induced or substance P agonist induced hyopermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The anti-inflammatory activity of the compounds of the present invention is demonstrated in the standard carrageenin-induced rat foot edema test [described by C. A. Winter et al., *Proceedings of the Society of Experimental Biology and Medicine*, Vol. 111, p. 544 (1962)]. In this test, anti-inflammatory activity is determined as the percent inhibition of edema formation in the hind paw of male albino rats (weighing 150–190 g) in response to a sub-plantar injection of carrageenin. The carrageenin is injected as a 1% aqueous solution. Edema formation is then assessed by measuring the volume of the injected paw initially as well as three hours after the carrageenin injection. The increase in volume three hours after carrageenin injection constitutes the individual response. Compounds are considered active if the difference in response between the drug-treated animals (six rats/group) and a control group receiving the vehicle alone is significant on comparison with the results afforded by a standard compound like phenylbutazone at 33 mg/kg, via the oral route of administration.

The present invention is illustrated by the following examples. It will be understood, however, that the invention is not limited to the specific details of these examples.

EXAMPLE 1

2-(Diphenylmethyl)-N-((2-methoxyphenyl)methyl)-1-azabicyclo[3.2.2]nonan-3-amine

A. 4-Cyano-N-carboethoxyperhydroazepine

To a 250 mL round-bottomed flask equipped with condenser and nitrogen inlet were added 4.34 g (23.49 mmol) N-carboethoxyperhydroazepin-4-one (prepared according to the procedure given by Z. G. Finney and T. N. Riley, *J. Med. Chem.*, 23, 895 (1980)), 10.53 g (54.02 mmol) tosylmethylisocyanide, and 117 mL 1,2-dimethoxyethane. The solution was cooled to 0° C., and 2.48 mL (54.02 mmol) ethanol and 9.21 g (82.2 mmol) potassium t-butoxide were added. The mixture was heated at 60° C. for 18 hours, cooled, and evaporated. The residue was taken up in ethyl acetate, washed with brine, dried over sodium sulfate, and concentrated to an oil. The oil was purified by chromatography on silica gel using hexane/ethyl acetate as eluent to afford 4.6 g (100%) of an oil.

$^1$H-NMR($\delta$,CDCl$_3$): 1.14 (t,J=5,6H), 1.8–2.0(m,6H),2.74 (m,1H), 3.2–3.5(m, 4H), 4.02 (quartets, J=5,4H).

IR(cm$^{-1}$, KBr): 2225 (CN), 1695 (CO).

$^{13}$C-NMR($\delta$, CDCl$_3$): 14.7, 25.2, 25.4, 29.1, 29.3, 29.4, 29.5, 31.7, 31.9, 43.3, 43.7, 45.7, 61.3, 121.6, 155.9, 156.0.

MS (%): 196 (53, parent), 123 (100), 56 (39).

Anal. Calc'd. for C$_{10}$H$_{16}$N$_2$O$_2$: C 61.20, H 8.22, N 14.127. Found: C 61.15, H 8.51, N 14.27.

B. Ethylperhydroazepine-4-carboxylate

To a 250 mL round-bottomed flask equipped with condenser and nitrogen inlet were added 4.6 g (23.5 mmol) 4-cyano-N-carboethoxyperhydroazepin-4-one and 100 mL 6N hydrochloric acid. The mixture was refluxed 18 for hours, cooled, and evaporated. The residue was taken up in 100 mL ethanol, saturated with hydrogen chloride gas and refluxed 36 hours. The reaction was cooled and evaporated, and the product characterized by mass spectrum before proceeding directly to the next step.

MS (%): 171 (11, parent), 101 (62), 86 (100), 56 (71).

C. Ethyl-N-ethoxycarbonylmethyl-perhydroazepine-4-carboxylate

The above compound (23.5 mmol) was dissolved in 120 mL ethanol, treated with 7.16 g (70.88 mmol) triethylamine and 5.92 g (35.44 mmol) ethyl bromoacetate, and refluxed for 2 hours. The reaction was cooled, evaporated, taken up in methylene chloride, washed with saturated aqueous sodium bicarbonate solution, dried over sodium sulfate and evaporated. The residue was chromatographed on silical gel using hexane/ethyl acetate as eluent to afford an oil, 4.17 g (69%).

$^1$H NMR ($\delta$, CDCl$_3$): 1.13 (t, J=6, 3H), 1.15 (t, J=6, 3H), 1.5–1.9 (m, 6H), 2.48 (m, 1H), 2.6–2.8 (m, 4H), 3.25 (m, 2H), 4.04 (quartets, 4H).

IR (cm$^{-1}$, KBr): 1735 (CO).

$^{13}$C-NMR ($\delta$, CDCl$_3$): 14.1, 14.2, 26.9, 29.5, 30.9, 43.6, 52.7, 54.9, 59.5, 60.0, 60.2, 171.3, 176.2.

MS (%): 257 (4, parent), 212 (10), 185 (16), 184 (100).

Anal. Calc'd. for C$_{13}$H$_{23}$NO$_4$: C 60.68, H 9.01, N 5.44. Found: C 60.22, H 9.12, N 5.57.

D. 1-Azabicyclo[3.2.2]nonan-3-one

To a 250 mL round-bottomed flask equipped with condenser and nitrogen inlet were added 1.55 g (39.69 g-atm.) potassium and 80 mL toluene. The mixture was heated to reflux and treated with 1.83 mL (39.69 mmol) ethanol. Refluxing continued until the potassium disappeared. Then 4.08 g (15.87 mmol) ethyl-N-ethoxycarbonylmethyl-perhydroazepine-4-carboxylate was added and refluxing was continued for 14 hours. The reaction was evaporated and the residue taken up in 100 mL 1N hydrochloric acid. This solution was refluxed for 22 hours, cooled, washed with methylene chloride, and adjusted to pH 12 with 6N sodium hydroxide. The aqueous layer was extracted with methylene chloride, which was dried over sodium sulfate and evaporated. The resulting foam, 700 mg (32%), was used directly below.

E. 2-(Phenylmethylene)-1-azabicyclo[3.2.2]nonan-3-one

To a 50 mL round-bottomed flask equipped with condenser and nitrogen inlet were added the title compound from step D (5.04 mmol), 40 mg (1.01 mmol) sodium hydroxide, 800 mg (7.55 mmol) benzaldehyde, and 13 mL ethanol. The solution was refluxed for 30 minutes, cooled, and evaporated. The residue was dissolved in methylene chloride, washed with water and brine, dried over sodium sulfate and evaporated. The residue was chromotographed on silica gel using hexane/ethyl acetate as eluent to afford an oil, 1.02 g (89%).

$^1$H-NMR ($\delta$, CDCl$_3$): 1.5–1.7 (m, 1H), 1.75 (m, 2H), 1.8–2.0 (m, 2H), 2.1–2.2 (m, 1H), 2.73 (m, 1H), 2.9–3.1 (m, 3H), 3.2–3.3 (m, 1H), 7.01 (s, 1H), 7.01 (s, 1H), 7.2–7.4 (m, 3H), 7.9 (m, 2H).

IR (cm$^{-1}$, KBr): 1705 (CO) and 1620 (C=C).

$^{13}$C-NMR ($\delta$, CDCl$_3$): 24.4, 26.5, 28.6, 44.6, 45.0, 56.3, 125.4, 128.5, 129.2, 131.4, 134.2, 145.8, 204.6.

MS (%): 227 (100, parent), 171 (86), 170 (81), 55 (54).

Anal. Calc'd. for C$_{15}$H$_{17}$NO·0.25H$_2$O: C 77.72, H 7.62, N 6.04. Found: C 77.90, H 7.36, N 5.99.

F. 2-(Diphenylmethyl)-1-azabicyclo[3.2.2]nonan-3-one

To a 100 mL round-bottomed flask equipped with nitrogen inlet were added 2 mL (5.84 mmol) of a 3 M solution of phenylmagnesium bromide in ether and 35 mL toluene. The solution was cooled to 0° C., and a solution of 1.02 g (4.49 mmol) 2-(phenylmethylene)-1-azabicyclo[3.2.2]nonane-3-one in 10 mL toluene was added. The reaction was stirred at 0° C. for 1 hour and quenched with saturated aqueous ammonium chloride. The organic layer was diluted with ethyl acetate, washed with saturated aqueous ammonium chloride solution until it was clear, dried over sodium sulfate, and evaporated. The residue was chromatographed on silica gel using hexane/ethyl acetate as eluent to afford an oil, 209 mg (16%; the 1,2 addition product accounted for about 40% of the reaction).

$^1$H-NMR ($\delta$, CDCl$_3$): 1.5–2.0 (m, 6H), 2.64 (m, 2H), 2.6–2.8 (m, 1H), 3.0–3.2 (m, 2H), 3.93 (d, J=8, 1H), 4.47 (d, J=8, 1H), 7.0–7.4 (m, 10H).

IR (cm$^{-1}$, KBr): 1720 (CO). $^{13}$C-NMR ($\delta$, CDCl$_3$): 24.1, 24.7, 26.0, 29.4, 30.0, 41.3, 46.0, 46.5, 48.0, 49.7, 5.06, 51.5, 58.9, 70.2, 72.7, 126.5, 128.1, 128.3, 128.4, 128.5, 128.7, 142.2, 142.7.

MS (%): 305 (3, parent), 277 (100), 110 (94), 91 (47).

G. 2-Diphenylmethyl-N-((2-methoxyphenyl)methyl)-1-azabicyclo[3.2.2]-nonan-3-amine To a 20 mL round-bottomed flask equipped with condenser and nitrogen inlet were added 209 mg (0.685 mmol) 2-(diphenylmethyl)-1-azabicyclo[3.2.2]nonan-3-one, 141 mg (1.03 mmol) 2-methoxybenzylamine, 2 mg camphorsulfonic acid, 3Å molecular sieves, and 4 mL toluene. The solution was refluxed for 22 hours, cooled, decanted from the sieves and evaporated. The residue was taken up in 0.5 mL tetrahydrofuran and treated with 2.7 mL (1.37 mmol) of a 0.5 M solution of 9borabicyclo[3.3.1]nonane in tetrahydrofuran and stirred at room temperature for 7 days. The reaction mixture was taken up in methyelene chloride, washed with 1N hydrochloric acid, and the aqueous layer adjusted to pH 12 with 6N aqueous sodium hydroxide and extracted with methylene chloride. The organic layer was dried over sodium sulfate, evaporated, and chromatographed on silica gel using methanol/methylene chloride as eluent to afford an oil, which was converted to its hydrochloride salt using HCl in ether, affording a white solid, mp 170–190° C. 29 mg (8%).

$^1$H-NMR ($\delta$, CDCl$_3$): 1.5–1.7 (m, 3H), 1.7–1.9 (m, 3H), 2.21 (m, 1H), 2.6 (m, 1H), 2.7 (m, 1H), 2.84 (m, 1H), 2.95 (m, 1H), 3.2 and 3.6 (m, 2H), 3.25 (m, 1H), 3.63 (s, 3H), 3.94 (dd, J=7.7,11.3, 1H), 4.34 (d, J=11.3, 1H), 6.6–7.4 (m, 14H).

IR (cm$^{-1}$, KBr): 1620 (C=C).

$^{13}$C-NMR (67, CDCl$_3$): 21.7, 25.2, 25.4, 28.9, 30.0, 41.8, 46.3, 51.3, 55.34, 57.4, 59.5, 63.9, 110.1, 120.3, 125.5, 126.1, 127.7, 127.96 127.04, 128.2, 128.34, 128.37, 128.42, 128.47, 128.52, 128.6, 128.8, 129.00, 129.07, 129.14, 129.6, 129.7, 143.0, 145.8, 157.3.

MS (%): 427 (2, parent+1), 260 (39), 259 (100), 121 (74), 110 (41), 91 (55).

Anal. Calc'd. for $C_{29}H_{34}N_2O \cdot 2HCl \cdot H_2O$: C 67.30, H 7.40, N 5.41. Found: C 67.11, H 7.21, N 5.18.

The title compounds of Examples 2–4 were prepared by a procedure analogous to that described in Example 1.

EXAMPLE 2

2-Diphenylmethyl)-N-((2-chlorophenyl)methyl)-1-azabicyclo[3.2.2.]nonan-3-amine

The title compound was prepared in 12% yield, as a dihydrochloride salt, mp 214–218° C.

$^1$H-NMR (δ, CDCl$_3$): 1.3–2.0 (m, 6H), 2.39 (m, 1H), 2.59 (m, 1H), 2.70 (m, 1H), 2.85 (m, 1H), 2.96 (m, 1H), 3.23 (m, 1H), 3.41 (dd, J=12, 134, 2H), 3.99 (m, 1H), 4.29 (d, J=10, 1H), 6.57 and 7.0–7.4 (m, 14H).

IR (cm.$^{-1}$, KBr): 1695, 1560 (C=C).

$^{13}$C-NMR (δ, CDCl$_3$): 21.8, 25.2, 28.8, 30.2, 41.9, 49.5, 51.4, 57.8, 59.5, 64.0, 125.5, 126.3, 126.6, 127.8, 127.9, 128.0, 128.9, 129.2, 130.1, 133.7, 137.7, 143.0, 145.6.

MS (%): 431 (1, parent), 265 (50), 263 (96), 140 (100), 125 (62), 110 (58).

Anal. Calc'd. for $C_{28}H_{31}N_2Cl \cdot 2HCL \cdot 2.5H_2O$: C 61.26, H 6.98, N 5.10. Found: C 61.06, H 6.76, N 4.20.

EXAMPLE 3

2-(Diphenylmethyl)-N-((2,4-dimethoxyphenyl)methyl)-1-azabicyclo[3.2.2]nonan-3-amine.

The title compound was prepared in 10% yield, as a dihydrochloride salt, mp 230–245° C.

$^1$H-NMR (δ, CDCl$_3$): 1.5–2.0 (m, 6H), 2.42 (m, 1H), 2.60 (m, 1H), 2.69 (m, 1H), 2.84 (m, 1H), 2.95 (m, 1H), 3.25 (m, 1H), 3.31 (dd, J=13,126,2H), 3.61 (s, 3H), 3.79 (s, 3H), 3.95 (dd, J=7,12, 1H), 4.37 (d, J=12, 1H), 6.3, 6.5 and 7.0–7.4 (m, 13H).

IR (cm.$^{-1}$, KBr): 1620, 1590, 1570 (C=C).

$^{13}$C-NMR (δ, CDCl$_3$): 21.8, 25.3, 29.0, 30.0, 41.8, 51.3, 55.3, 55.4, 57.4, 59.5, 63.8, 103.8, 125.4, 126.1, 127.8, 128.0, 128.1, 128.8, 130.2, 143.0, 145.9, 158.3, 159.7.

Anal. Calc'd. for $C_{30}H_{36}N_2O_2 \cdot 21$ HCl$\cdot$3.5H$_2$O: C 61.27, H 7.63, N 4.76. Found: C 61.20, H 7.45, N 4.63.

EXAMPLE 4

2-Bis(4-Fluorophenyl)methyl)-N-((2-methoxyphenyl)methyl)-1-azabicyclo[3.2.2]nonan-3-amine The title compound was prepared in 12% yield, as a dihydrochloride salt, mp 170–180° C.

$^1$H-NMR (δ, CDCl$_3$): 1.4–2.0 (m, 6H), 2.40 (m, 1H, 2.45 (m, 1H), 2.63 (m, 1H), 2.76 (m, 1H), 2.84 (m, 1H), 3.10 (m, 1h), 3.31 (dd, J=13,130, 2H), 3.62 (s, 3H), 3.71 (dd, J=7,12, 1H), 6.6–7.2 (m, 12H).

IR (cm.$^{-1}$, KBr): 1610 (C=C).

$^{13}$C-NMR (δ, CDCl$_3$): 21.7, 25.2, 28.9, 30.0, 41.7, 46.7, 49.6, 55.2, 57.2, 59.5, 64.4, 110.1, 114.5, 114.8, 115.3, 115.6, 120.2, 128.0, 128.3, 129.3, 129.4, 129.6, 129.7, 138.68, 138.72, 141.4, 157.4, 159.6, 162.5, 162.9.

Anal. Calc'd. for $C_{29}H_{32}N_2OF_2 \cdot 2HCl \cdot 1.5H_2O$; C 61.92, H 6.63, N 4.98. Found: C 61.86, H 6.91, N 4.89.

EXAMPLE 5.

2-((4-Fluorophenyl)methylene)-1-azabicyclo[3.2.2]nonan-3-one

The title compound was prepared by a procedure analogous to that described in Example 1E in 98% yield, as a yellow oil.

$^1$H-NMR (δ, CDCl$_3$): 1.5–2.3 (m, 6H), 2.77 (m, 1H), 2.9–3.3 (m, 4H), 6.9–7.1 and 7.8–8.0 (m, 4H), 7.24 (s, 1H).

IR (cm.$^{-1}$, KBr): 1700 (C=O).

MS (%): 245 (100, parent), 216 (75), 189 (83), 188 (74), 121 (38), 55 (43).

High Res. MS: Calc'd. for $C_{15}H_{16}NOF$: 245.1197. Found: 245:1222.

EXAMPLE 6

2-(Bis(4-Fluorophenyl)methyl)-1-azabicyclo[3.2.2]nonan-3-amine

The title compound was prepared by a procedure analogous to that described in Example 1F.

$^1$H-NMR (δ, CDCl$_3$): 1.6–2.1 (m, 6H), 2.6–2.7 (m, 3H), 3.1–3.3 (m, 2H), 3.95 (d, J=9, 1H), 4.49 (d, J=9, 1H), 6.9–7.0 and 7.2–7.4 (m, 8H).

IR (cm.$^{-1}$), KBr): 1705 (C=O).

$^{13}$C-NMR (δ, CDCl$_3$): 24.0, 26.1, 29.2, 41.4, 46.5, 49.6, 59.0, 70.3, 115.0, 115.2, 115.3, 129.8, 130.0, 130.1, 137.7, 137.8, 138.4, 138.5, 159.9, 160.0, 163.1, 163.2, 216.5.

MS (%): 341 (1, parent), 313 (62), 110 (100), 109 (56), 82 (46).

Anal. Calc'd. for $C_{21}H_{21}NOF_2$: C 73.88, H 6.20, N 4.10. Found: C 74.04, H 6.12, N 4.10.

I claim:

1. A compound of the formula

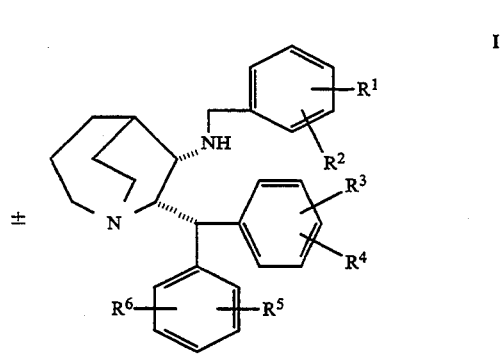

wherein R$^1$, R$^2$, R$^3$, R$^4$, R$^5$ and R$^6$ are each independently selected from hydrogen, fluorine, chlorine, bromine, trifluoromethyl, alkyl having from one to three carbon atoms, alkoxy having from one to three carbon atoms, carboxy, alkoxycarbonyl having from one to three carbon atoms in the alkoxy moiety and benzoyloxycarbonyl; or a pharmaceutically acceptable salt thereof.

2. A compound according to claim 1 wherein R$^1$ is methoxy and each of R$^2$, R$^3$, R$^4$, R$^5$ and R$^6$ is hydrogen.

3. A compound according to claim 2 wherein R$^1$ is 2-methoxy.

4. A pharmaceutical composition for treating or preventing a condition selected from the group consisting of inflammatory diseases, anxiety, colitis, depression or dysthymic disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising an amount of a compound according to claim 1 effective in preventing or treating such condition and a pharmaceutically acceptable carrier.

5. A method of treating or preventing a condition selected from the group consisting of inflammatory diseases anxiety, colitis, depression or dysthymic disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising administering to a mammal in need of such treatment of prevention an amount of a compound according to claim 1 effective in preventing or treating such condition.

6. A pharmaceutical composition for antagonizing the effects of substance P in a mammal, comprising a substance P antagonizing effective amount of a compound according to claim 1 and a pharmaceutically acceptable carrier.

7. A method of antagonizing the effects of substance P in a mammal, comprising administering to said mammal a substance P antagonizing effective amount of a compound according to claim 1.

8. A pharmaceutical composition for treating or preventing a condition in a mammal, the treatment or prevention of which is effected or facilitated by a decrease in substance P mediated neurotransmission, comprising an amount of a compound according to claim 1 effective in antagonizing the effect of substance P at its receptor site and a pharmaceutically acceptable carrier.

9. A method of treating or preventing a condition in a mammal, the treatment or prevention of which is effected or facilitated by a decrease in substance P mediated neurotransmission, comprising administering to a mammal in need of such treatment or prevention an amount of a compound according to claim 1, or a pharmaceutically acceptable salt thereof, effective in antagonizing the effect of substance P at its receptor site.

10. A pharmaceutical composition for treating or preventing a condition in a mammal, the treatment or prevention of which is effected or facilitated by a decrease in substance P mediated neurotransmission, comprising an amount of a compound according to claim 1, or a pharmaceutically acceptable salt thereof, effective in treating or preventing such condition and a pharmaceutically acceptable carrier.

11. A method of treating or preventing a condition in mammal, the treatment or prevention of which is effected or facilitated by a decrease in substance P mediated neurotransmission, comprising administering to a mammal in need of such treatment or prevention an amount of a compound according to claim 1 effective in treating or preventing such condition.

* * * * *